United States Patent
Casadó Galcerá

(12) 
(10) Patent No.: US 6,447,762 B1
(45) Date of Patent: Sep. 10, 2002

(54) HAIR LOTION USEFUL FOR TREATMENT OF HAIR LOSS AND STIMULATING HAIR GROWTH

(75) Inventor: Francesc Casadó Galcerá, Barcelona (ES)

(73) Assignee: Colomer Group Spain, S.L., Barcelona (ES)

( * ) Notice: Subject to any disclaimer, the term of this patent is extended or adjusted under 35 U.S.C. 154(b) by 0 days.

(21) Appl. No.: 09/487,971

(22) Filed: Jan. 20, 2000

(30) Foreign Application Priority Data

Jan. 29, 1999 (ES) .................................. 9900190

(51) Int. Cl.[7] .............................. A61K 7/06; A61K 6/00; A61K 7/00
(52) U.S. Cl. .................... 424/70.1; 424/401; 514/63; 514/880
(58) Field of Search .................. 424/401, 70.1; 514/63, 880

(56) References Cited

U.S. PATENT DOCUMENTS 6,114,325 A * 9/2000 Fukunishi et al.
6,172,250 B1 * 1/2001 Seguin et al.

* cited by examiner

*Primary Examiner*—Thurman K. Page
*Assistant Examiner*—Humera N. Sheikh
(74) *Attorney, Agent, or Firm*—Ladas & Parry

(57) ABSTRACT

A hair lotion with improved properties in its hair protecting action and prevention of hair loss, and the reduction of external effects of androgenic alopecia and resulting hair loss, that comprises as an active ingredient a mixture consisting of: i) hop extract (*Humulus lupulus*), ii) rosemary extract (*Rosmarinus officinalis* L.), iii) Swertia extract (*Swertia japonica*) and iv) silanodiol salicylate; the remaining ingredients consisting of a cosmetically and pharmaceutically acceptable medium, in general an alcohol or hydroalcohol medium that can contain other auxiliary ingredients, such as vitamins, colorants, fragrances and similar substances.

12 Claims, No Drawings

HAIR LOTION USEFUL FOR TREATMENT OF HAIR LOSS AND STIMULATING HAIR GROWTH

The present invention relates to a hair lotion with properties that prevent hair loss and stimulate hair growth. The peculiarity of the hair lotion object of the invention lies in the synergic effect arising from the interaction of its four active ingredients, consisting of three plant extracts and a synthetic organosilicic compound.

Alopecia, colloquially known as baldness, strictly speaking cannot be considered as a disease but rather a biological dysfunction which produces a feeling of discomfort and/or uneasiness in the affected individual, which may even lead to serious psychological disorders. The most common form is androgenic alopecia, which, among the mammals, affects chimpanzees, orangutans, and other primates, as well as men.

It is estimated that the number of hairs in man varies on average between 100,000 and 150,000, with a loss of 50 to 100 hairs a day being considered normal. It is understood that to avoid baldness it is important to maintain the average number of hairs, that is, to maintain the hair cycle, whereby the hair is formed, grows and falls out before being replaced by another new hair that appears in the same follicle.

The most common of the various classes of alopecia is androgenic alopecia which, as indicated by its name, is induced by androgenic stimulation of the hair follicles and is influenced by genetic and age factors. In this type of baldness testosterone, the best-known male hormone produced by the genital organs, plays an important role, although it is not the only substance involved. However, 50% of circulating testosterone is produced by peripheral tissues. It is known that in the hair follicle the enzyme 5-alpha-reductase (also called testosterone-reductase) converts the testosterone into dihydrotestosterone (DHT), which has a more powerful action than testesterone, which accumulates in the follicular cell membrane, reducing its functionality and accordingly retarding the hair growth.

It is a known fact that the upper part of the scalp responds to androgens in a different way to the rest of the body. On the other hand, it is paradoxical that the production of androgens from puberty onwards favours hair growth in areas of the body that develop terminal hair (beard, chest, armpits, calves) and at the same time reduce the growth of hair at the vertex (upper part of the scalp). The cause of this unexplainable paradox probably lies in the genetic difference in hormonal-type response determined by different receptor tissue specificity according to the zone implicated.

In women, the presence of high estrogen amounts (female hormones) inhibits the effect of androgens, which counteracts the effects of the androgens on the base of the hair bulb. As a result, the arrival of the menopause with subsequent reduction in female hormone levels, means that the circulating androgens have the upper hand, and so can set off an alopecic symptomatology similar to that seen in males. Thus, an hormonal approach explains why alopecic phenomena appear just after puberty in males while in females they do not manifest themselves until after the reproductive capacity of the individual has extinguished and biological maturity reached.

The first histological change that occurs is the appearance of degenerative foci in the sheath of the follicle connective tissue with the resulting basophilic perivascular change. The follicle progressively contracts, leaving behind a sclerotic and hyaline filament of connective tissue. Nevertheless, even in scalp areas where the follicles have shrunk, and therefore produce a very small vellus, there are still a reduced number of static terminal follicles, whose growth would be possible to try to stimulate. Androgenic alopecia is a very widespread condition, particularly in its least severe forms.

Other factors that facilitate the complex phenomenon of hair loss, besides hormones are:
  ageing of the follicle cells by external aggressions and lack of care
  deficiency in nutrition of the hair by progressive reduction in the micro-circulation in the scalp
  weak growth of the hair cells which reproduce more slowly and with lower numbers.

Other aetiologies of alopecia, which are mentioned for informative purposes only, as they do not fall within those treated by the hair lotion object of the invention are, among others: a) temporal alopecia caused by the administration of drugs of different types, the most well known being those derived from the administration of anti-cancer products; b) alopecia of nutritional or metabolic origin; c) alopecia caused by alterations to the central nervous system; d) alopecia areata consisting on the sudden disappearance of hear from one or several areas of the scalp, due to an alteration in the immunological system whereby the follicle is attacked by the lymphocytes and the anagen stage is suddenly interrupted.

For many years now, and in order to satisfy an ever growing demand in today's society in which personal image is a very important factor for many people, the cosmetic industry has been investigating hair compositions that reduce, and ideally eliminate, the effect of alopecia, and more specifically, induce or facilitate hair growth.

The applicant firm, after a long and complex investigation has found a new hair lotion, whose essential characteristic is the specific nature of its four active ingredients, three of which are of vegetal origin and the fourth is of synthetic origin, more specifically an organosilicic compound. The three ingredients of vegetal origin are:
  i) hop extract (*Humulus lupulus*),
  ii) rosemary extract (*Rosmarinus officinalis* L.),
  iii) Swertia extract (*Swertia japonica*) and the fourth compound is
  iv) silanodiol salicilate.

The rest of the ingredients of the formulation are formed by a cosmetically acceptable medium, in general an alcohol or hydroalcohol medium which can contain other auxiliary ingredients, such as vitamins, colorants, fragrances, etc.

Rosemary (*Rosmarinus officinalis*) is a shrub-like plant of the Lamiaceae family, which reaches up to a metre in height with narrow leaves with a whitish underside. Its flowers are liliaceous or white-coloured. The extract used in the lotion of the invention, which contains a wide variety of molecular species, is an hydroalcohol (50% alcohol) extract of the leaves of the plant with a 7–10% w/w concentration of dry material 7–10% w/w. There are numerous studies which have shown that rosemary extract acts in two basic biochemical ways in the complex phenomenon that underlie alopecia:
  It protects the cell membranes that help to neutralise the action of free radicals generated by numerous uncontrolled oxidation reactions that take place in the tissues.
  It inhibits the formation of the dihydrotestosterone (DHT) directly implicated in alopecia, as explained above.

The hops (*Humulus lupulus*) is a plant of the cannabinacea family. The main industrial use of this plant is in the manufacture of beer. The hops oil mainly contains terpenes and humulene [(E,E,E)-2,6,6,9-tetramethyl-1,4,8-cycloundecatriene]. An hydroalcohol lotion is used in the lotion of the present invention which act as:

an inhibitor of the activity of the 5-alpha-reductase (type I) enzyme responsible for the formation of DHT, which is the main hormone responsible for hair loss in androgenic alopecia, an activator of keratinocyte proliferation, an anti-oxidant inhibitor of free radicals, slightly less effective than the rosemary extract.

Of the wide variety of families of the Swertia plant, in the hair lotion of the present invention *Swertia japonica* is used, concretely a glycol extract with a swertiamarin content not lower than 3% (w/w). This plant is widely accepted in Japan, both for internal and external use, for the treatment of a wide variety of diseases. In studies carried out by S. Utsunomiya, T. Nishiura and Y. Hagihara in the Department of Dermatology of the Tokushima University (Japan) it has been shown that thanks to the direct stimulation of the hair follicles and activation of blood circulation to the hair roots, the extract favours the oxygen and nutrients supply to the base of the follicle, revitalising the hair cells, which translates into a stimulation of hair growth.

Silanodiol salicylate is a biologically active silicon compound which is described in the International Patent Publication WO 96/10574 as follows: 2,2-dimethyl-4-oxobenzo-1,3-dioxa-2-silane Stabilizer: salicyclic acid

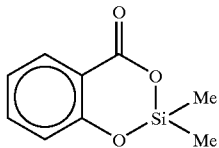

The silicon along with carbon is the most abundant chemical element in nature. In trace quantities it plays an important role in biological systems and is present in the epidermis and the cuticle of hair where it acts to increase the chemical resistance of keratin by participating in the reticulation of the collagen fibres and accordingly in restructuring the hair contributing mainly to an increase in the resistance of the hair shaft. In addition to the action of the silicon in biological systems in general, several documents have been published which show its importance in the regulation of the physiological cycle of the hair and as a dermal papilla cytostimulant.

The three main properties of silicon, of great usefulness in the hair treatments are:

Restructuring/hydrating effects, because it binds to proteins and other hydrating substances allowing the scalp to retain the necessary degree of humidity and to avoid dehydration.

Cytostimulant of the dermal and hair follicle cells.

Anti free-radical element which reorganises the cell membranes, making them more resistant to attack by these free radicals and therefore to ageing.

The problem of supplying silicon to biological systems consists in finding a way that can be assimilated by the organism in opposition to elemental silicon or silicones. A silicon compound that satisfies this requirement is silanodiol salicylate which, together with the three vegetal extracts mentioned hereinabove, has been seen to be particularly suitable as a hair-protection and growth-promotion agent.

The applicant firm understands that the interaction of silanodiol salicylate (which, of the four active ingredients, is the one used in least amount) with different molecular species contained in the extracts of the three plants mentioned hereinabove that form the rest of the active ingredients, provokes a tonic and protective effect against the causes of androgenic alopecia when applied to the scalp. This leads to a reduction in hair loss, and in the case that the hair follicles have not become completely atrophied, a re-growth of new hair may occur. These effects are demonstrated in the trial carried out with 40 volunteers. This trial is described in more detail later in the Examples.

A brief examination of the various attempts in the art to find an efficient cosmetic composition to control hair loss and stimulating growth is now made.

SU 488559 (UKRBYTKHIM FIRM) which relates to a hair conditioner that prevents hair loss and the formation of dandruff, which contains extracts with carbonate of the warmwood plant, glycerine, emulsifier and water. With regards with the present invention it should be pointed out that this patent only mentions one (hop extract) of the four active ingredients which the lotion object of the invention contains.

JP 40022598 (SHIGEKURA), whose title is: "Gentian Extracts" describes a process for obtaining extracts from the gentian plant from which it is said that they have a tonic action and stimulate hair growth, and that they are also effective for treating hepatic ailments and cancerous growths. Furthermore, properties of cardiac stimulation are attributed to them, and cosmetic uses for the skin. Among the wide variety of additional ingredients that can be incorporated into these extracts the extract of the Japanese Swertia plant is mentioned.

JP 40018281 (OGIHARA) relates to a process for obtaining an ester of acetic acid and an ingredient extracted from gentian plants, such as *Swertia chinensis, Swertia tosaenis*, etc (which the express exclusion of *Swertia japonica*). It is said of the acetate obtained that it is used as an agent for accelerating hair growth or as a skin cosmetic. As the japonica variety is expressly excluded, it can be concluded that this Japanese patent is not related to the object of the present application. As can be appreciated the active ingredient of this patent has a mixed character between a net vegetal component and synthetic compound component.

CA 672965 (HAGIWARA) relates to a nutritive or restorative hair composition that comprises at least one of the bitter components of the *Swertia japonica* Makino plant and a non-toxic diluent. In addition to the hair nutritive or restorative properties which are mentioned in the document, anti-seborrheic and anti-pruritic properties are also attributed to it.

FR 2129804 (SLATCHO) is directed at "Detaining hair loss using a cream or lotion that contains camphor and lard". Among other ingredients found in the cream or lotion rosemary extract can be found.

FR 1545601 (PEREIRA-BORGES-MARQUES M) relates to an anti-dandruff lotion which contains extracts of rosemary and eucalyptus leaves, bone marrow and bay salt. In addition to only containing one of the active ingredients of the lotion of the present invention, it is not expressly directed at controlling hair loss and enhancing hair growth, but indirectly through controlling dandruff.

JP 05051308 (FUKUDA HIDECO) describes the treatment of hair with a solution whose active ingredients consist exclusively of components of different herbs among which rosemary and *Swertia japonica* can be found.

JP 09175950 (DAIICHI SEIYAKU CO. LTD.) specifically describes preparations for stimulating hair growth that contain stabilised carpronium chloride and plant extracts, among which rosemary and *Swertia japonica* are mentioned.

JP 09183718 (KOSEI CO LTD) relates to cosmetic compositions for external use, whose main active ingredients are phytic acid and/or salts thereof. As optional ingredients extracts of rosemary and Swertia japonica are mentioned.

EP-0797984 (belonging to the firm SISHEIDO COMPANY LIMITED and claiming priority from the Japanese application 97105058) describes a composition, among whose ingredients extracts of rosemary and Swertia are found, and although it is specifically directed to controlling ageing of the skin, it also has a utility as a hair tonic as it acts on the zone which surrounds the hairs.

JP 10059829 (NOEVIR CO, LTD) has as an object hair tonics containing nutrients encapsulated in lipids. Rosemary and hop extracts are among the various mentioned ingredients.

JP 07196456 (SUNSTAR KK) has as an object the hair preparations that contains copolymers of vinylpyrrolidone and plant extracts, among which those of rosemary and hops are mentioned then having the same relation with the lotion of the present invention as that of the Japanese patent cited in the previous paragraph.

CH 682631 (V. FORGACS, K. PACZOLAY, G. PINTZ and JP TATAR) describes compositions that promote hair growth that contain herbal components such as nettle, pansy and chickweed as the main components, citing hop and rosemary extracts as other optional ingredients.

SU 1247011 (AEROSOL SCIENTIFIC-INDUSTRIAL ENTERPRISES) describes, just as the two previous patents, hair compositions among whose ingredients hop and rosemary extracts are mentioned.

U.S. Pat. No. 4,933,177 (L'OREAL) describes cosmetic compositions for hair and skin treatment in the form of dust particles, the relation to the lotion of the present invention being that rosemary is found among the ingredients of the composition.

JP 09241131 (NENDO KAGAKU KENKYUSHO KK) describes agents which promote hair growth, among whose ingredients hops and Swertia japonica are found.

U.S. Pat. No. 5,656,264 (SANSYO SEIYAKU CO, LTD) relates to a method for promoting hair growth by application of a composition whose main ingredients are of synthetic nature, among which compounds of diphenyl-urea, pyrimidine derivatives, imidazole compounds, benzoylaminourea compounds and compounds of aminopyrrolo [2,3-d]-pyrimidine can be found. In said patent it is indicated that the previous compounds can be used with other ingredients among which rosemary is cited.

U.S. Pat. No. 5,053,222 (SHISEDO COMPANY LTD) describes a cosmetic composition for hair care whose main active ingredients are a diester of phosphoric acid with ascorbic acid and tocopherol. Among other optional ingredients extracts of diverse plants are mentioned, among which rosemary is cited.

EP 0872228 (KAO CORPORATION) relates to cosmetic methods that employ compositions whose active ingredients are exclusively of vegetal origin, among which rosemary and Swertia extracts are cited.

JP 10152426 (KANEBO LTD) has as an object skin conditioning compositions that contain urea as an essential ingredient, and diverse products derived from plants among which those from rosemary, hops and Swertia are cited.

JP 07277939 (DOWA MINING CO) relates to topical preparations, of anti-ageing cosmetic use, which contain active oxygen, anti-oxidants, and other biologically active substances, among which extracts of rosemary, hops an Swertia japonica are cited.

U.S. Pat. No. 4,919,.846 (SHISEIDO COMPANY LTD) protects a detergent composition which contains a quaternary ammonium cationic surfactant and a carboxylate anionic surfactant. Said composition, which has a utility as a shampoo, and not as an anti-hair loss or hair-growth promoter lotion, can have other non-essential ingredients such as extracts of Swertia japonica, rosemary and hops.

From the point of view of synthetic compounds with anti-hair loss and/or hair growth promoter activity, MINOXIDIL (whose chemical name is 6-(1-piperidinyl)-2, 4-pyrimidinediamine 3-oxide, U.S. Pat. No. 3,644,364) is well known. It was initially used in therapy al hypotensor. When hypertensive patients noticed an unexpected hair growth, advantage was taken of this side effect, and for a certain period it was used as a hair regenerator such that in Spain the "Vademecun Internacional" of 1997 lists the pharmaceutical product "LACOVIN", consisting of a 2% hydroalcohol solution containing propylene glycol. However, because even when applied topically it acted as a hypotensive agent it has been banned by the European Union as a cosmetic product due to the danger of its use by hypotensive patients. Similarly, its pharmaceutical use as an oral hypotensive agent has been rejected, due both to its secondary effects and because it has been surpassed by new families of hypotensive agents.

With regards patent application WO /10574 (PCT/FR 95/01267), in which the preparation of a family of biologically active silicon compounds is described, among which silanodiol salicylate is found, it should be noted that only in Example 5 of said patent an anti-hair loss lotion is described. However, said lotion has the peculiarities of: a) using silyl-pantenol as specific compound (different to methyl salicylate); b) using a quantity (4%) very much higher than that of the silicon compound used in the present invention (<0.1%); and c) being destined to control seborrheic alopecia.

Reviewing the prior art it is deduced that the hair lotion of the invention is not anticipated by the compositions that have tried to solve the problem of alopecia. In addition to its excellent properties the lotion of the invention have the advantage of using the synthetic silicon ingredient in minimal quantities, less than 0.1%, by weight, which for practical purposes allows it to be classed as an ecological cosmetic composition.

From the quantitative point of view, the hair lotion of the invention has the following composition:

Active Ingredient
  (three extracts+Si compound) . . . 2 to 6% w/w
  Rest of ingredients . . . 98 to 94% w/w.

The proportion of the four components of the active ingredient is such that it complies with the ratio:

$$L > R > Sw > Ssi$$

where:
  L—% of hop extract
  R—% of rosemary extract
  Sw—% of Swertia extract
  Ssi—% of silanodiol salicylate
with the preferred values, relative to the total weight of active components, being the following:
  L . . . 55–65% weight/weight
  R . . . 25–35% weight/weight
  Sw . . . 7–10% weight/weight
  Ssi . . . 1–2% weight/weight.

For the lotion object of the invention to produce results, an intensive programmed of daily application of an ampoule containing a single-dose of 6 ml for at least 6 weeks, is necessary.

It is very desirable that the intensive treatment is followed by a maintenance programme of 3 6-ml ampoules every other day for 2 months.

In cases of severe alopecia, the intensive treatment should be extended for a further 2 months, and then the maintenance programme followed in identical way.

It is highly advisable that before applying the hair lotion object of the invention, the hair is washed 2 or 3 times a week with a suitable shampoo of a pH of approximately 5.5. Then, after drying the hair with a towel the content of the ampoule is applied by gentle massage to favour absorption and to facilitate irrigation of the scalp.

The invention is illustrated by the following Examples which are only intended for illustrative purposes and are not limiting.

EXAMPLE 1

Using usual methods in cosmetics a batch of 10 kg of a lotion of the invention is prepared with the following composition:

| Component | Amount in grams | % W/W |
|---|---|---|
| Denaturised alcohol | 2700 | 27.00 |
| Hydrogenated oxyethylenated castor oil | 150 | 1.50 |
| Fragrance | 175 | 1.75 |
| Deionised water | 6640 | 66.40 |
| Swertia extract | 25 | 0.25 |
| Silanodiol salicylate | 7 | 0.07 |
| Hop extract | 210 | 2.10 |
| Rosemary extract | 85 | 0.85 |
| Panthenol | 8 | 0.08 |
| Total | 10000 | 100.00 |

EXAMPLE 2

Following the same process as in Example 1, another formulation was prepared in accordance with the invention with the following composition per 100 g.

Rosemary extract . . . 1.1 g

Hop extract . . . 1.8 g

Swertia extract . . . 0.25 g

Silanodiol salicylate . . . 0.04 g

Ethyl alcohol . . . 32 g

Water, s.q.ad . . . 100 g

Evaluation of the Properties of the Lotion of the Invention

To evaluate the in vitro efficacy of the hair lotion object of the invention, a method has been developed for determining the inhibitory action exerted by said lotion on the activity of the 5-alpha-reductase (type I) enzyme responsible for the formation of dihyrdotestosterone (DHT) en the follicle cells.

It has been demonstrated that the hop and rosemary extracts used act as efficient inhibitors of the enzyme, reducing its activity between 50% and 80% of that observed in absence of the inhibitor.

To evaluate the efficacy of the hair lotion object of the invention against hair loss an assay has been carried out in which the efficacy of the product of the invention denominated Con. 628 and a comparative product denominated Con. 749 were studied. 40 volunteers (20 men and 20 women) who were suffering either from androgenic alopecia or telogen elluvious took part in the study. Each individual randomly received one of the two products and was shown how to apply the product to the scalp in accordance with the defined method twice a day for 6 months.

Before the start of the study (time t0) and after 2, 4 and 6 months of treatment dermatological ascertainments and instrumental evaluations were carried out. Photricograms of 9 defined area of the scalp were carried out at the beginning and at the end of the treatment.

The results obtained with the two products are shown in he following table:

| Con. 749 (without organic extracts or organosilicic compound | Con. 623 (Lotion of the invention) |
|---|---|
| An improvement was appreciated, which was not statistically significant to traction of the resistance of the anagenic hair | A statistically significant improvement in the resistance of the anagenic hair to traction was appreciated after four months of treatment and at the end of the treatment ($P < 0.05$). |
| A progressive resolution of the clinical signs associated with hair loss were appreciated (seborrhea and dandruff). The reduction in the values of the clinical rating related to the two signs was not statistically significant at any time during the study | A progressive resolution of the two clinical signs associated with hair loss (seborrhea and dandruff) were appreciated. The reduction of the values of the clinical rating related to dandruff is statistically significant after four and six months of treatment ($p < 0.05$). |
| A non-statistically significant reduction in the amount of hair loss per wash at the end of the treatment was observed | A statistically significant reduction in the amount of hair loss per wash at the end of the treatment was observed ($p < 0.05$) |
| An increase in the micro-circulation of the scalp was observed at the end of the treatment, line of significant separation ($p = 0.05$) | A statistically significant increase in the micro-circulation of scalp at the end of the treatment was appreciated ($p < 0.05$) |
| A statistically significant reduction in the sebometric values after 4 months and after 6 months of treatment was observed ($p < 0.05$). | A statistically significant reduction in the sebometric values after four months ($p = 0.01$) and after six months ($p < 0.051$) was observed. |
| A 10.8% statistically significant increase in new hair growth at the end of the trial ($p < 0.05$) expressed as average of hair density per unit surface area was observed | A 22.4% statistically significant increase in new hair growth at the end of the trial ($p < 0.05$) expressed as average of hair density per unit surface area was observed. |

-continued

| Con. 749 (without organic extracts or organosilicic compound | Con. 623 (Lotion of the invention) |
|---|---|
| A statistically significant increase in rapid hair growth (anagenic) and a statistically significant reduction in slow hair growth (telegeny) was observed at the end of the treatment (p < 0.05) An 8% increase in the A/T ratio (anagen/telegen), statistically representative, was appreciated at the end of the treatment. | A statistically significant increase in rapid hair growth (anagenic) and a statistically significant reduction in slow hair growth (telegeny) was observed at the end of the treatment (p < 0.05) An 20% increase in the A/T ratio (anagen/telegen), statistically representative, was appreciated at the end of the treatment |

Subjective Determination After Treatment

At the end of the treatment each patient from a group of 20 was asked to give his or her opinion (personal impression) on the efficacy of the product of the invention against hair loss on the following four-point scale.

0—No efficacy
1—Little efficacy
2—Moderate efficacy
3—High efficacy

The results are shown in the following table

|  | 0 | 1 | 2 | 3 |
|---|---|---|---|---|
| Cod. 749 | — | 5 (25%) | 14 (70%) | 1 (5%) |
| Cod. 628 | — | 3 (15%) | 13 (65%) | 4 (20%) |

Product Tolerance

No signs related with local intolerance were observed during treatment. Some patients reported a reduction in seborrhea and an increase in the dryness of the scalp for the trial products.

What is claimed is:

1. A hair lotion comprising a mixture of active ingredients, including (i) hop extract (*Humulus lupulus*), (ii) rosemary extract (*Rosmarinus officinalis* L.), (iii) swertia extract (*Swertia japonica*) and (iv) silanodiol salicylate, in a cosmetically acceptable medium, said active ingredients being present in the hair lotion in respective amounts effective for prevention or treatment of hair loss or promotion of hair growth in a user.

2. The hair lotion according to claim 1, wherein the active ingredients are present in respective amounts that satisfy the following relationship: hop extract>rosemary extract>swertia extract>silanodiol salicylate.

3. The hair lotion according to claim 1, wherein the active ingredients are present in the lotion in respective amounts as follows:

hop extract . . . 55–65% weight/weight rosemary extract . . . 25–35% weight/weight

*Swertia japonica* extract . . . 7–10% weight/weight

Silanodiol salicylate . . . 1–2% weight/weight.

4. The hair lotion according to claim 3, wherein the active ingredients (i), (ii), (iii), and (iv) comprise 2 to 6% weight/weight of all ingredients in the hair lotion.

5. The hair lotion according to claim 4, wherein the medium comprises an alcohol or hydroalcohol.

6. The hair lotion according to claim 5, wherein the medium comprises ethyl alcohol.

7. The hair lotion according to claim 5, wherein the medium further comprises an auxiliary ingredient or ingredients selected from the group consisting of vitamins, colorants and fragrances.

8. The hair lotion according to claim 7, wherein the medium comprises panthenol.

9. A method for prevention or treatment of hair loss in a user comprising administering to the user the hair lotion of claim 1 in an amount effective to prevent or treat hair loss.

10. A method for prevention or treatment of hair loss in a user comprising administering to the user the hair lotion of claim 4 in an amount effective to prevent or treat hair loss.

11. A method for promotion of hair growth in a user comprising administering to the user the hair lotion of claim 1 in an amount effective to promote hair growth.

12. A method for promotion of hair growth in a user comprising administering to the user the hair lotion of claim 4 in an amount effective to promote hair growth.

* * * * *